US005632754A

United States Patent [19]
Farley et al.

[11] Patent Number: 5,632,754
[45] Date of Patent: May 27, 1997

[54] UNIVERSAL CATHETER WITH INTERCHANGEABLE WORK ELEMENT

[75] Inventors: Brian Farley, Los Altos; Ron R. Hundertmark, San Mateo; Grace Y. Schulz, San Carlos, all of Calif.

[73] Assignee: Devices for Vascular Intervention, Santa Clara, Calif.

[21] Appl. No.: 363,142

[22] Filed: Dec. 23, 1994

[51] Int. Cl.$^6$ ................................................. A61D 17/32
[52] U.S. Cl. ............................ 606/159; 606/170; 606/180; 604/22
[58] Field of Search .............................. 606/155, 170, 606/171, 180; 604/22

[56] References Cited

U.S. PATENT DOCUMENTS 3,732,858  5/1973  Banko ........................................ 604/22

FOREIGN PATENT DOCUMENTS 9112773  9/1991  WIPO ........................................ 606/159

*Primary Examiner*—Michael Powell Buiz
*Assistant Examiner*—William Lewis
*Attorney, Agent, or Firm*—Douglas A. Chaikin, Esq.; Peninsula IP Group

[57] ABSTRACT

Disclosed herein is an intravascular universal catheter having interchangeable work elements and methods of use thereof. The catheter comprises a flexible catheter body having a distal end, a proximal end and a lumen extending between the ends. A housing having an open interior and an aperture on a lateral side is attached to the distal end of the catheter body by a coupling element. A work element is movably disposed within the housing and operative through the aperture. A work element connector is disposed in a lumen of the catheter body and has a distal end connected to the work element. At least the distal portion of the lumen defines a receiving space within the catheter body, and the coupling element is configured to allow retraction of the work element from the housing through the open proximal end into the receiving space. In a preferred embodiment, perfusion ports are disposed in the catheter body and the housing proximate to the junctional region of the catheter body with the housing. The perfusion ports are in communication with the lumen. The work element may be withdrawn from the housing proximal to the perfusion ports to allow blood to flow into the housing and bypass the work element for perfusion of tissue downstream. Preferably, the lumen is configured to allow the work element to be completely withdrawn from the catheter body, so as to permit interchange of various work elements.

26 Claims, 5 Drawing Sheets

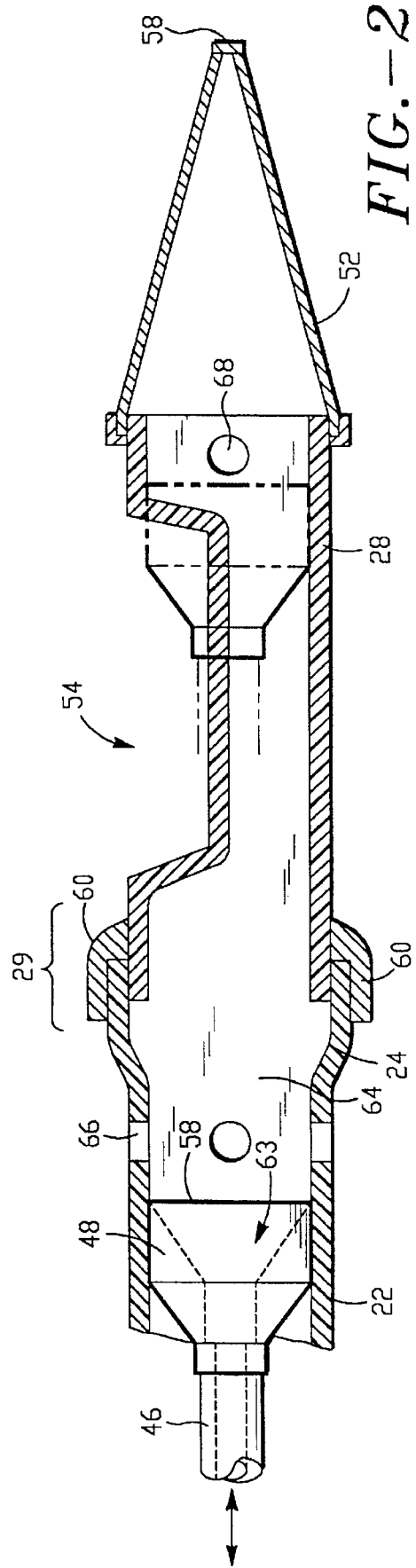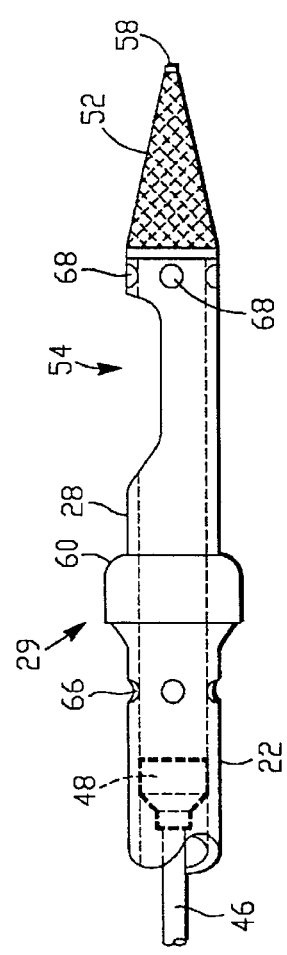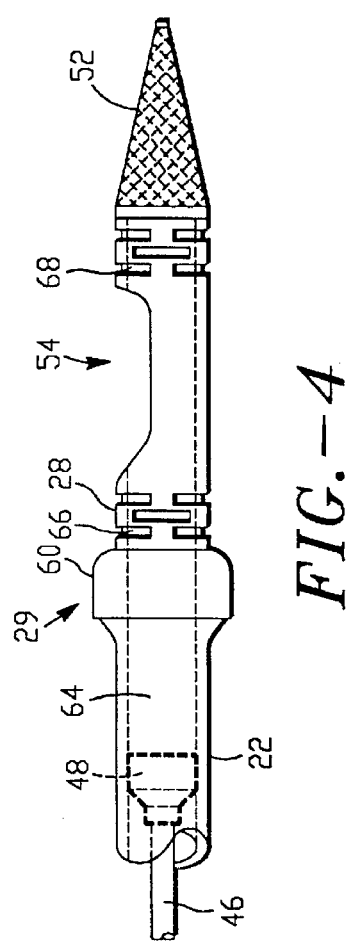

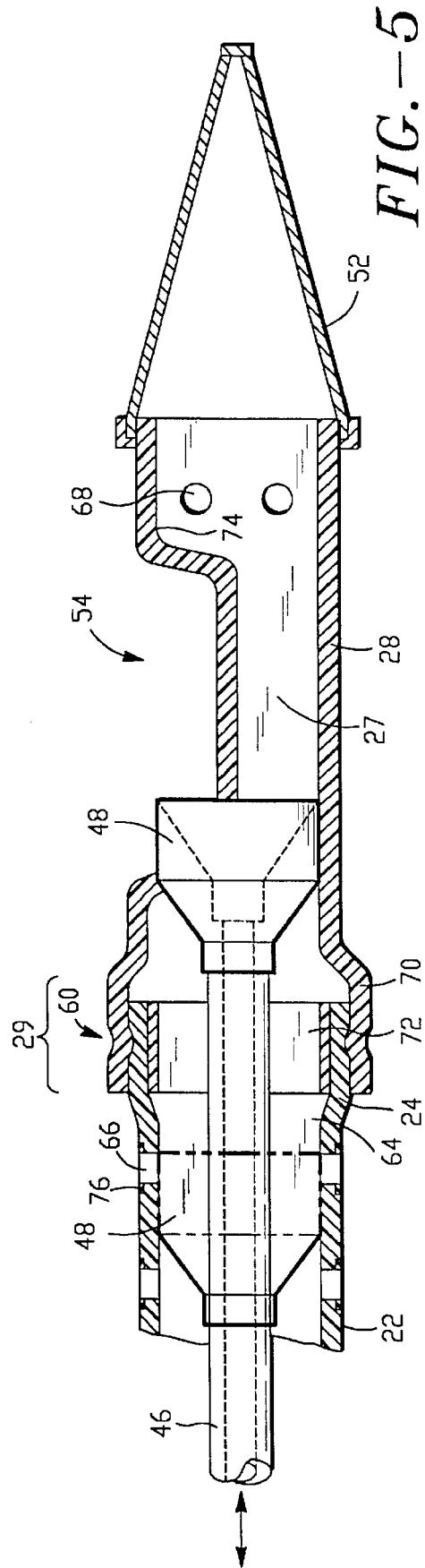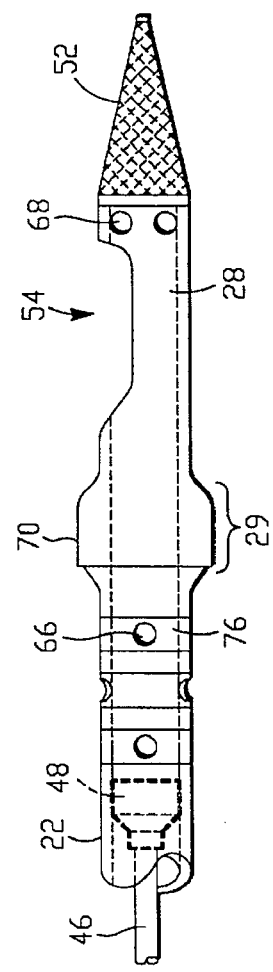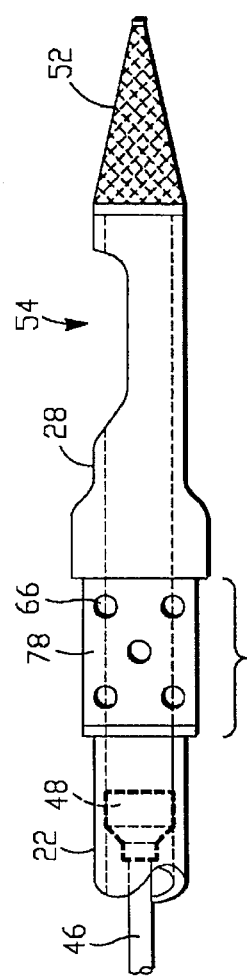

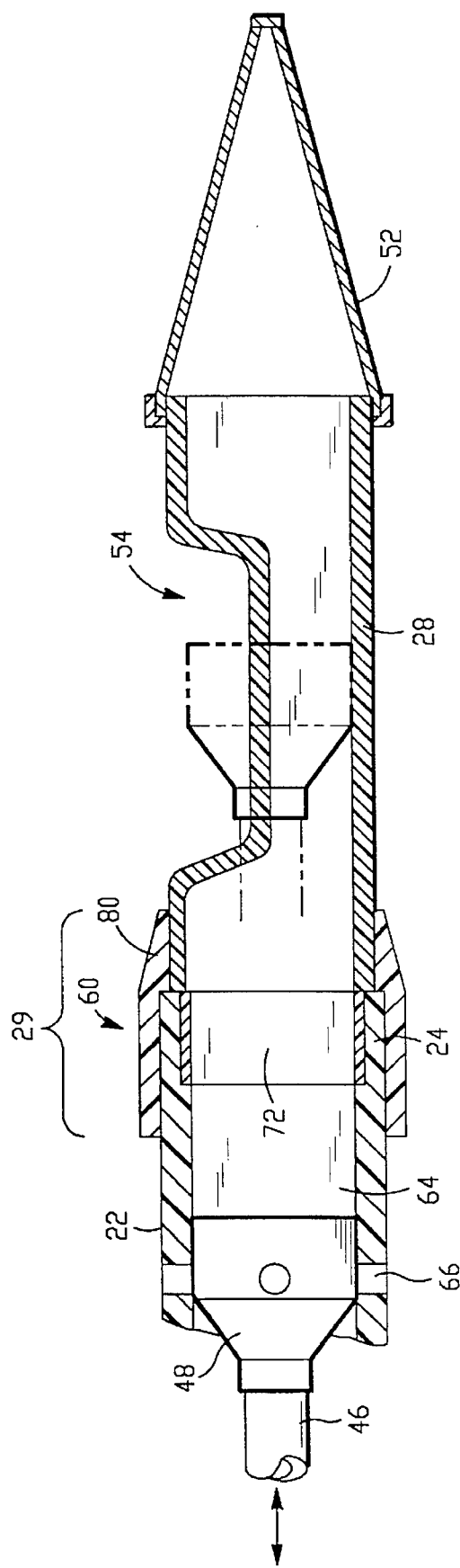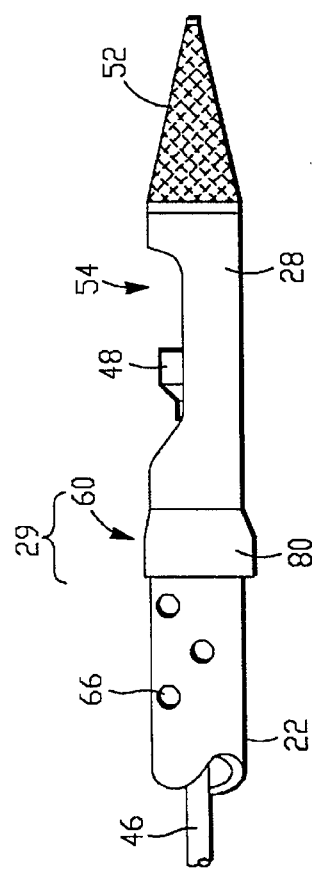
FIG.-8
FIG.-9

UNIVERSAL CATHETER WITH INTERCHANGEABLE WORK ELEMENT

RELATED APPLICATION

This application contains subject matter related to the following patent and applications: U.S. Ser. No. 08/357,999 (Attorney Docket No. DEVI1476); U.S. Pat. No. 5,507,795 (Attorney Docket No. DEVI1464); and U.S. Ser. No. 08/224,169 (Attorney Docket No. DEVI1467). The full disclosure of each of these applications is incorporated herein by reference.

BACKGROUND OF THE INVENTION

1. Field of Invention

The present invention relates generally to the construction and use of vascular and other catheters. More particularly, the invention relates to intravascular catheters with a housing and a window on a lateral side of the housing for surgical intervention within a biological conduit.

2. Previous Art

Arteriosclerosis, also known as atherosclerosis, is a common human ailment arising from the deposition of fat-like substances, referred to as atheroma or plaque, on the walls of blood vessels. Such deposits occur both in peripheral blood vessels that feed the limbs of the body and in coronary blood vessels that feed the heart. When deposits accumulate in localized regions of a blood vessel, the regions become stenosed, blood flow is restricted, and the person's health is at serious risk.

Numerous approaches for reducing and removing such stenotic deposits have been proposed, including balloon angioplasty, where a balloon-tipped catheter is used to dilate the stenosed region, atherectomy, where a blade or other cutting element is used to sever and remove stenotic material, and laser angioplasty, where laser energy is used to ablate at least a portion of the stenotic material.

Typically, while using an atherectomy catheter a cutting blade is advanced past an opening in a housing at the distal end of a vascular catheter. By positioning the housing so that at least a portion of the stenotic material passes through the opening, the stenotic material can be severed and translated forward by advancing the cutting blade. Typically, such cutting blades are circular, and are rotated and advanced simultaneously to affect the desired cutting.

Atherectomy catheters are described in U.S. Pat. Nos. 4,669,469; 4,781,186; 4,926,858; 4,979,951; 5,047,040; 5,084,010; and reissued U.S. Pat. No. Re. 33,569. Of these, the U.S. Pat. Nos. 4,926,858 and 5,047,040 patents describe atherectomy catheters having rotating cutters which are extended distally through an opening in the distal end of a housing to penetrate and/or remove stenotic material in the vessel. The U.S. Pat. No. 4,979,951 and U.S. Pat. No. Re. 33,569 patents describe catheters having distal housings where a rotatable cutting blade receives a coaxial movable guidewire. U.S. Pat. No. 4,781,186 describes atherectomy catheters having flexible distal housing. Co-pending application Ser. No. 07/821,905, now abandoned assigned to the assignee of the present application, describes an atherectomy catheter having a flexible nose cone attached to the distal end of a cutter housing.

The atherectomy catheters disclosed above have enjoyed widespread success in both peripheral and coronary applications. However, in known atherectomy catheters, the curing blade cannot be withdrawn proximally from the housing due to various factors including the connection structures used for connecting the housing to the distal end of the catheter body, as well as clearance limitations in the interior of the catheter body. Situations arise in which it would be desirable to withdraw the curing blade from the housing while leaving the catheter body and distal housing positioned in the vessel.

For example, if the vessel lumen becomes blocked by a combination of stenosis and the catheter housing, it is desirable to withdraw the cutter from the housing in order to provide blood bypass through the device for perfusion of tissue downstream of the catheter. In another example, the work element may need to be replaced before the task is finished. Moreover, there are situations in which it would be desirable to completely withdraw the curing blade from the catheter, for purposes such as exchanging the cutter for a different type of work element to perform other interventional procedures such as imaging, drug delivery, dilatation, laser ablation and the like. If it is desired to perform more than one procedure at a treatment site, atherectomy catheters presently in use require that the catheter, including the catheter body, be entirely withdrawn from the vessel and replaced and repositioned with an entirely new catheter having the desired type of work element.

For these and other reasons, catheter designs are desired of the type in which a housing is attached to the distal end of a catheter body, the housing has a window for directional intervention in a biological conduit. In particular, it is desirable to allow the housing to be positioned in a biological conduit to have its related work element interchanged without removing the housing. It would be desirable for such an improved catheter to include a flow bypass for flowing blood through the housing with the work element in place, for perfusion of tissue downstream of the work element. Such an improved catheter should permit the work element to be withdrawn from the housing into a receiving space in the catheter body. Most desirably, such an improved catheter permits the work element to be completely withdrawn from the proximal end of the catheter body, to allow interchange of various work elements, such as rotating and reciprocating cutters, abrasive grinding elements, dilatation devices, ultrasonic and angioscopic imaging devices and laser ablation devices, ultrasonic or mechanical vibrating elements that alter vessel compliance, among others.

SUMMARY OF THE INVENTION

It is an object of this invention to provide an intravascular catheter that can be left in place within a blood vessel while the work element of the catheter is partially withdrawn to permit blood flow.

It is an additional object of this invention to provide an intravascular catheter that can be left in place within a blood vessel while the work element can be fully withdrawn from the catheter.

It is yet an additional object of this invention to provide an intravascular catheter that can be left in place within a blood vessel while the work element can be exchanged for another work element.

It is a further object of this invention to provide an intravascular catheter that is capable of performing a multiplicity of surgical interventions.

It is also an object of this invention to provide methods of surgical intervention within a blood vessel using a universal catheter with an interchangeable work element.

Finally, it is another object of this invention to provide methods of surgical intervention within a blood vessel using a single catheter to perform several types of interventions.

In accordance with the above objects and those that will be mentioned and will become apparent below, the universal catheter with interchangeable work element of the present invention comprises:

a catheter body having a distal end, a proximal end and a lumen extending therebetween; and a housing having a hollow interior, an aperture on a lateral side thereof, and an open proximal end connected to the distal end of the catheter body, the connection defining a junctional region; and the lumen of the catheter body and the hollow interior of the housing combining to create a receiving space, whereby a work element can be inserted into the receiving space from the proximal end of the catheter body.

In accordance with the above objects and those that will be mentioned and will become apparent below, the method of surgically intervening within a blood vessel comprising the steps of:

providing a universal catheter that includes:

a catheter body having a distal end, a proximal end and a lumen extending therebetween; and, a housing having a hollow interior, an aperture on a lateral side thereof, and an open proximal end connected to the distal end of the catheter body, the connection defining a junctional region, and the lumen of the catheter body and the hollow interior of the housing combining to create a receiving space for a work element;

selecting a first work element;

inserting the first work element into the receiving space from the proximal end of the catheter body;

inserting the universal catheter from its distal end into and along the blood vessel lumen until the aperture of the housing is opposing a site of interest; and, operating the first work element.

In an exemplary embodiment of the device, the catheter includes a work element within the housing and attached to a work element connector disposed within a lumen of the catheter body and extending to the proximal end of the catheter body.

In another exemplary embodiment the work element is a rotary atheroma cutting device and the work element connector defines a drive cable.

In yet another exemplary embodiment the catheter has at least one perfusion port in the catheter body or housing proximate to the junctional region and the receiving space provides for retraction of the work element proximal to the perfusion port thereby allowing for perfusion of tissue downstream from the catheter.

In an exemplary embodiment of the method of surgical intervention, insertion of the catheter within the blood vessel is preceded by insertion of a guidewire within the blood vessel proximate to the region of interest, followed by positioning the catheter within the blood vessel by sliding the catheter distally along the guidewire with the guidewire passing through an internal lumen of the catheter body.

In another exemplary embodiment of the method, a first work element is used to perform a first interventional procedure. It is then removed while the catheter body and housing remain in place. A second work element is inserted within the housing and a second interventional procedure is performed.

It is an advantage of the present invention to provide a catheter with interchangeable work elements and methods by which the universal catheter can be used.

It is an advantage that the work element can be withdrawn from the housing or from the entire catheter, while the catheter body and housing remain positioned in a biological conduit.

Furthermore, it may be desirable to perform various procedures at a particular treatment site, including imaging, dilatation (angioplasty), laser ablation, or atherectomy. Catheters and methods presently in use require the entire catheter to be withdrawn and a different device positioned at the treatment site in order to perform a multi-task surgical procedure.

It is a particular advantage of the universal catheter of the present invention that the catheter body and housing may remain in position in a vessel while various work elements are interchanged and operated through the aperture in the housing.

The presence of the catheter, and particularly the housing at its distal end, occupies a significant portion of the vessel lumen. Where stenosis has caused narrowing of the vessel lumen, the housing may occlude substantially all of the remaining open portion of the vessel lumen. For this reason, it is a further advantage of the catheter of the instant invention to provide a blood perfusion bypass system whereby blood is allowed to flow through the housing to perfuse tissue downstream of the catheter. This allows the physician more time to position the catheter and facilitates extended treatment without creating an ischemic reaction in the patient.

BRIEF DESCRIPTION OF THE DRAWING

For a further understanding of the objects and advantages of the present invention, reference should be had to the following detailed description, taken in conjunction with the accompanying drawings, in which like parts are given like reference numerals and wherein:

FIG. 2 is a side cross-sectional view of an embodiment of the housing and a distal portion of the catheter body of universal catheter with interchangeable atheroma cutter.

FIGS. 3 and 4 are side elevational views of alternative embodiments of the housing and a distal portion of the catheter body illustrating perfusion ports.

FIGS. 5 and 6 are side cross-sectional and full views respectively of the housing and a distal portion of the catheter body of the universal catheter with interchangeable work element in a profusion embodiment.

FIG. 7 is a side elevational view of the distal portion of the catheter illustrating another profusion embodiment.

FIGS. 8 and 9 are side cross-sectional and full views respectively of a distal portion of the universal catheter with interchangeable work element in another profusion embodiment.

DETAILED DESCRIPTION OF THE INVENTION

Figure 1:
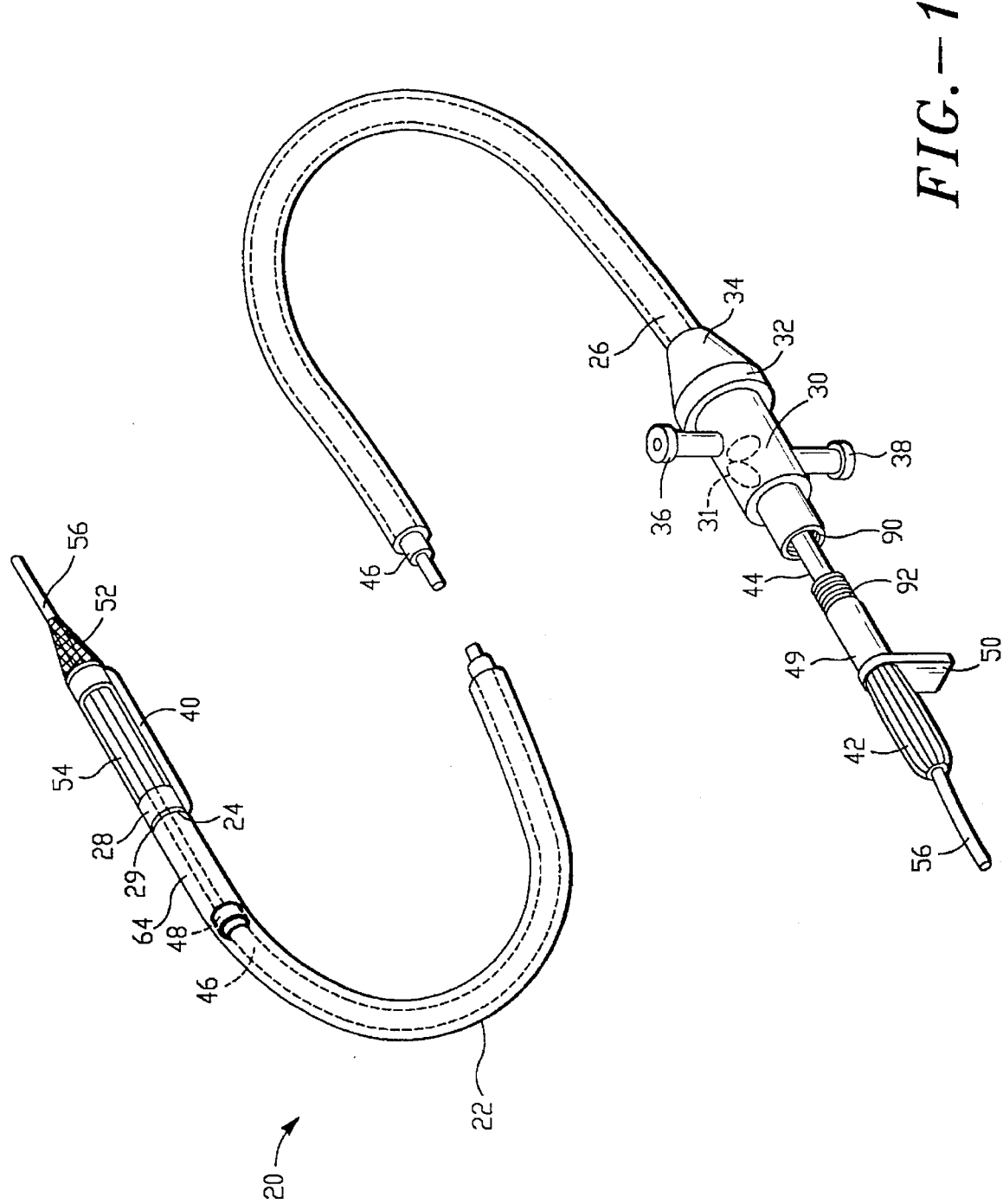
FIG. 1 is a perspective view of a universal catheter with interchangeable work element constructed in accordance with the principles of the present invention.

According to the present invention, a catheter comprises an elongated catheter body having a distal end, a proximal end, and an axial lumen therebetween. The catheter also includes a housing having a hollow interior, an open proximal end, a distal end and an aperture on a lateral side of the housing. A coupling element is provided for connecting the distal end of the catheter body to the proximal end of the housing. A work element is movably disposed in the housing and operative through the aperture. A work element connector is disposed in a lumen of the catheter body, preferably the axial lumen, and has a distal end connected to the work element. The proximal end of the connector is available at the proximal end of the catheter body for attachment to a device appropriate for the operation of the work element.

Operationally, the distal portion of the catheter is inserted within a blood vessel of a subject and the proximal portion of the catheter remains external to the subject. The work element performs its particular task upon a portion of the blood vessel while in place within the housing, but the work element is operated from the proximal end of the catheter, external to the patient. The work element connector transduces the particular mechanical, electrical, chemical, or optical signal that is appropriate to the function of the work element from the proximal operator end to the work element for operation. It is to be understood that, each type of work element and work element connector is operated in a manner that is unique to the function and design of the particular type of work element.

The operation of a variety of these work elements and connectors are well known to those skilled in the art. For example, a cutting device such as a rotary atheroma cutter (work element) is attached to a drive cable (work element connector) which in turn passes through the proximal assembly and is connected to a motor drive unit (device). Operation of the motor drive unit along with axial translation of the rotary cutter results in severing of the atheroma.

Similarly, a wide variety of work elements (and work element connectors) such as cutting blades (and drive cables) for performing atherectomy procedures, heated elements (electrical wires) for performing thermal ablation, electrodes (electrical wires) for performing electrosurgical cutting and cauterization, abrasive elements for performing mechanical ablation (drive cables), optical waveguides (fiber optic lines) for performing laser ablation, ultrasonic transducers (ultrasonic transduction lines) for imaging and ablation, angioscopic imaging devices (fiber optic lines) and the like perform their particular task within the housing of the catheter, but are operated in a particular fashion from the proximal end of the catheter.

The universal catheter provides for the performance of these various intravascular procedures without the need to completely withdraw each device and reposition another at the treatment site for each new procedure.

At least a distal portion of the axial lumen in the catheter body defines a receiving space, and the coupling element is configured to allow retraction of the work element from the housing and into the receiving space by axially translating the work element connector through the open proximal end. This allows bypass flow of blood for perfusion. In a preferred embodiment the receiving space spans a lumen of the catheter body, from distal to proximal end, and provides for the removal of the work element from the catheter for interchange of various types of work elements.

The work element in an alternative embodiments comprises a rotatable blade, an abrasive element, an ultrasonic transducer, an angioscopic imaging device, a laser ablation device, and the like.

Referring now to the drawings, a number of embodiments of the universal catheter with interchangeable work element constructed in accordance with the present invention will be described. In all the embodiments shown in the drawings the work element is a atheroma cutter and the work element connector is a drive cable. However, these embodiments are merely exemplary and a wide variety of other specific implementations of the present invention may also be accomplished within the spirit and scope of this invention.

FIG. 1 illustrates an embodiment of the universal catheter with an interchangeable work element and a work element connector. The universal catheter is generally indicated by the numeral 20 and includes a guidewire 56, a nose cone 52, a housing 28, a junctional region 29, a catheter body 22 with a lumen 64, a work element 48, a work element connector 46, and a proximal assembly 30.

The flexible catheter body 22 has a distal end 24, a proximal end 26 and the lumen 64 therebetween. The housing 28 with an elongated aperture 54 is attached to the distal end 24, and the attachment defines the junctional region 29. The nose cone 52 is attached to the distal end of the housing 28. The proximal assembly 30, used for operating the catheter and work element while it is within the blood vessel, is attached to the proximal end 26 of the catheter body 22. A hemostasis valve 31 such as a flange or hinged flap can be located in proximal assembly 30 to prevent backbleeding when the work element and connector are withdrawn.

The work element 48 is inserted into the catheter through the lumen 64 of the catheter body 22 from the proximal end 26 of the catheter body 22 and, for task operation upon a blood vessel, the work element 48 is positioned in a hollow interior of the housing 28 opposed to the aperture 54. The work element connector 46 is secured to the work element 48 and axially advances the work element 48 through the catheter body 22. When the work element 48 is in an operating position within the housing 28, the work element connector 46 spans the entire length of the catheter body 22 within the lumen 64. The work element 48 and the connector 46 each preferably has an axial lumen (not shown) through which the guidewire 56 also passes.

Operationally, stenotic material is positioned through the aperture 54 and is severed by the axial translation of the work element 48 (a cutter) across the perture 54. A balloon 40, mounted to the housing 28 opposite the aperture 54 is inflated to urge the housing 28 against the stenotic region. The catheter 20 has the nose cone assembly 52 attached to the distal end of the housing 28. The nose cone assembly 52 may be a spring coil, a mesh, a polymeric tube or other flexible structure. The nose cone 52 serves to atraumatically guide the distal end of the housing 28 and serves to receive the severed stenotic material.

In an embodiment of the method, the guidewire 56 is inserted into the blood vessel prior to insertion of the catheter 20. The distal end of the movable guidewire 56 is positioned to lie proximate the region of interest within the vascular system. The universal catheter 20 is then introduced over the guidewire 56 and advanced. The guidewire 56 becomes positioned along the longitudinal axis of the catheter 20, through the hollow interior of the housing 28, the lumen 64 of the catheter body 22, and the proximal assembly 30. In this embodiment, the guidewire 56 passes through axial lumens of the work element 48, the work element connector 46, a drive shaft 44 and a spline 42.

In the embodiment shown in FIG. 1, the interchangeable work element 48 of the catheter 20 comprises an atherectomy cutter 48 and the work element connector 46 is a drive cable 46. The drive cable 46 is connected to the cutter 48 and provides for the operational rotation and the axial advancement of the cutter 48. FIG. 1 shows the cutter 48 retracted into the catheter body 22, but during performance of its operational task (the severing of atheroma from the interior wall of the blood vessel) the cutter is positioned in the housing 28 proximate to the aperture 54. During operation, the cutter 48 is mechanically rotated by means of a motor drive unit (not shown) such as that disclosed in U.S. Pat. No. 4,771,774, the disclosure of which is incorporated herein by reference. Several elements of this embodiment are specific for this particular work element. The drive cable 46 is attached to a drive shaft 44 with a spline 42 adapted for connection to the motor drive unit. The drive shaft 44 has an advance lever 50. The advance lever 50 is rotationally decoupled from the drive shaft 44 to permit manual translation of drive cable 46 and cutter 48 in the axial direction.

In this embodiment a proximal assembly 30 is suitably adapted for use with a rotary atheroma cutter work element. Also shown are a rotator ring 32 and transition element 34. The assembly 30 has a luer fitting 36, a flush port 38, a rear cap 92, and a rear opening 90.

The proximal end 26 of the catheter body 22 is secured to the interior of the rotator ring 32 which is rotatably coupled to the proximal assembly 30. The transition element 34 allows for flexion of the catheter body 22 relative to the proximal assembly 30. The luer fitting 36 of the proximal assembly 30 is in communication with the balloon 40 on the housing 28 through a lumen (not shown) in the catheter body 22. The housing balloon 40 is inflatable thereby. The catheter body lumen 64 is in communication with the flush port 38 of the proximal assembly 30 to provide connection of a perfusion or an aspiration source. The proximal assembly 30 has the rear opening 90 to which the rear cap 92 connects by threads or other known means. The drive shaft 44, connected to the drive cable 46, extends through the rear cap 92. During operation of the cutter 48, the rear cap 92 is engaged in the rear opening 90 of the proximal housing.

To withdraw the cutter 48 from the housing 28, the axial advance lever 50 is pulled in the proximal direction until the cutter has been withdrawn into the catheter body 28. If it is desired to withdraw the cutter entirely from the catheter body, the rear cap 92 may be decoupled from the rear opening 90, and the drive cable 46 along with the cutter 48 are withdrawn proximally through the catheter body lumen 64 and the rear opening 90.

Another work element, such as an ultrasonic imaging transducer, optical waveguide, angioscope, ultrasonic transducer, laser ablation device or the like, may be inserted through the rear opening 90 and the catheter body lumen 64 until the work element is positioned in the housing 28.

FIG. 2 illustrates an embodiment of the housing 28 and the distal end 24 of the catheter body 22. Also shown are the nose cone 52, the housing aperture 54, a coupling element (slip ring) 60, the junctional region 29, the work element (cutter) 48, the work element connector (drive cable) 46, and the catheter body lumen 64.

The distal end 24 of the catheter body 22 is flared so as to have an inner diameter larger than the outer diameter of the housing 28. The distal end 24 of the catheter body 22 extends over the proximal end of the housing 28 and is attached thereto by the coupling element 60. The coupling element 60 and an overlap of the catheter body 22 and the housing 28 define a junctional region 29 which has a definite length measured along a longitudinal axis of the catheter body 22 and the housing 28. In this embodiment, the coupling element comprises a slip ring 60 designed to compress the distal end of the catheter body against the exterior of the housing 28, by crimping, heat-shrinking or by other means known to those skilled in the art. The catheter body lumen 64 in the catheter body 22 is aligned with the open proximal end of the housing 28 such that the cutter 48 may be withdrawn through the open proximal end of the housing 28 and into the catheter body lumen 64. The lumen 64 and the hollow interior of the housing 28 define a receiving space for the work element 48. The cutter 48 is shown with an annular cutting edge 58 and an open interior space 63.

In a preferred embodiment, the catheter body lumen 64 has a diameter extending from the distal end 24 to the proximal end 26 (FIG. 1) which is larger than the outer diameter of the cutter 48, allowing the cutter to be withdrawn through the proximal end of the catheter body.

FIG. 3 is a side elevational view of an alternative embodiment of the housing 28 and a distal portion of the catheter body 22. FIG. 3 further illustrates the nose cone 52, the aperture 54, the outlet ports 68, the coupling element 60, the junctional region 29, the perfusion ports 66 and the work element (cutter) 48.

The perfusion ports 66 are provided proximate to the junctional region 29 in the catheter body 22. In the context of this invention the term "proximate to the junctional region" means within a distance equivalent to five lengths of the junctional region 29, preferably within two lengths. When the work element 48 is proximal to the perfusion ports, blood flows with less resistance into the catheter body lumen 64 (See FIG. 2) and distally into the housing 28. The exit ports 68 are provided in the housing 28 distal to the aperture 54 to increase facilitation of blood flow through the housing and perfuse tissue downstream from the catheter. The blood may also exit through a hole 58 in the distal end of the nose cone 52, usually configured to receive the movable guidewire 56 (FIG. 1).

FIG. 4 is a side elevational view of another embodiment of the present invention which includes a nose cone 52, a housing 28, an aperture 54, outlet ports 68, a coupling element 60, a junctional region 29, perfusion ports 66, a work element (cutter) 48, and a catheter body 22.

The perfusion ports 66 are provided in the housing 28 proximate to the junctional region 29 and proximal to the aperture 54. The perfusion ports 66 can have a variety of configurations, including rectangular slots as illustrated. Ordinarily, such slots are used where a more flexible housing is desired, since such slots increase the bendability of the housing 28. The exit ports 68 may alternatively comprise slots, as well as a variety of other structures. The cutter 48 may be withdrawn from the housing 28 proximal to the perfusion port 66, allowing blood to flow into the catheter body lumen 64 and the interior of the housing 28, from which blood may exit via the aperture 54, exit ports 68 or the nose cone 52 so as to perfuse tissue downstream of the device.

FIGS. 5 and 6 illustrate another embodiment of the present invention which includes a nose cone 52, a housing 28, an aperture 54, outlet ports 68, a coupling element 60, a junctional region 29, perfusion ports 66, a work element (cutter) 48, and a catheter body 22.

A proximal portion 70 of the housing 28 surrounds the distal portion 24 of the catheter body 22, and is connected to the exterior of the catheter body 22 by welding, adhesive, or other known means. An overlap of the housing 28 and the catheter body 22 define the junctional region 29. When the work element 48 is an atheroma cutter, it is usually desirable to support and guide the cutter in the housing 28 such that cutter engages stenotic material protruding through the aperture 54 and "parts off" material as the cutter slides under a parting surface 74 in the hollow interior 27 of the housing 28. For this purpose, the inner diameter of the housing 28 in the portion containing the aperture 54 is selected such that the cutter slidably engages the interior of the housing to be supported and guided thereby. Thus, as illustrated in FIG. 5, the housing 28 has an inner diameter which is larger in the proximal portion 70 than in the distal portion.

FIG. 7 is a side elevational view of another embodiment of the invention which includes a nose cone 52, a housing 28, an aperture 54, a transition section 78, a junctional region 29, perfusion ports 66, a work element (cutter) 48, and a catheter body 22.

Here, the flexible, tubular transition section 78 is connected to the proximal end of the housing 28 and to the distal end of the catheter body 22. In this embodiment the transition section 78 also defines the junctional region 29. The transition section 78 is made of a flexible material such as, for example, a superelastic alloy such as Nitinol®. The transition section 78 has an axial passage through which the cutter may be withdrawn into the catheter body 22. The perfusion ports 66 are disposed in the transition section 78 to allow blood to flow into the housing 28. The transition section 78 obviates the need to form perfusion ports 66 in the catheter body 22, thereby reducing manufacturing costs and maintaining the structural integrity of the distal portion of the catheter body.

FIGS. 8 and 9 illustrate an embodiment of the invention which includes a nose cone 52, a housing 28, an aperture 54, a coupling element 60, a support ring 72, a tubular adapter 80, a junctional region 29, perfusion ports 66, a work element (cutter) 48, and a catheter body 22.

The proximal end of the housing 28 is butted against the distal end 24 of the catheter body 22. The coupling element 60 includes the support ring 72 in the catheter body lumen 64 at the distal end of the catheter body and the tubular adapter 80. The tubular adapter 80 has a distal portion configured to receive the proximal end of the housing 28, and a proximal portion configured to receive the distal end of the catheter body 22. In this embodiment the tubular adapter 80 defines the junctional region 29, and is attached to the housing 28 and to the catheter body 22 by methods known in the art such as crimping, shrinking, use of adhesive, welding and the like.

As shown in FIG. 9, the perfusion ports 66 are provided proximate to the junctional region 29 and in communication with the catheter body lumen 64 (FIG. 8) to provide inflow of blood to the housing 28. The cutter may be withdrawn through the proximal end of the housing 28 and into the catheter body lumen 64 (FIG. 8) to a point proximal to the perfusion port 66. The blood may then flow into the housing 28 and exit through the aperture 54 or through the nose cone 52 to perfuse tissue downstream to the device.

Figure 10:
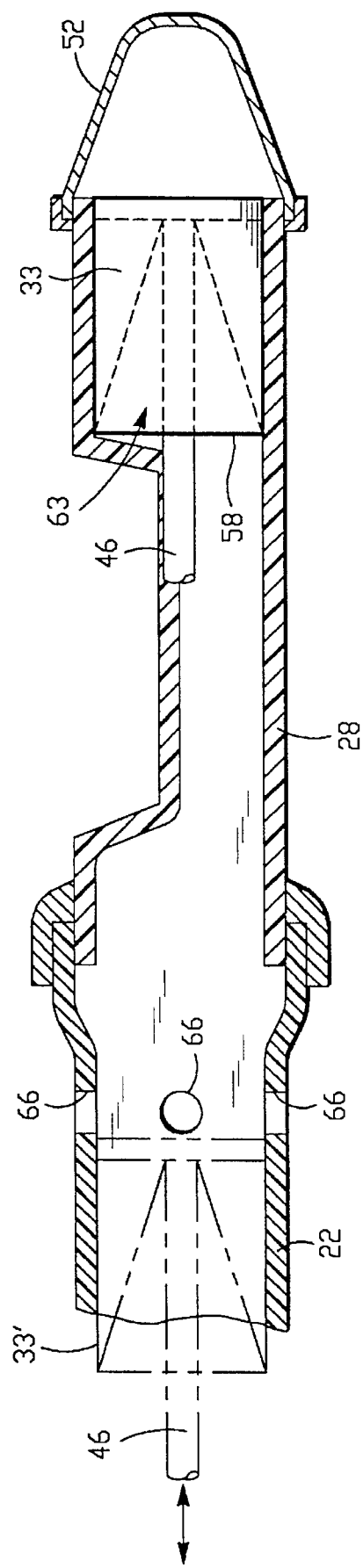
FIG. 10 is a side cross-sectional view of a catheter housing with a modified atheroma cutter.
Figure 11:
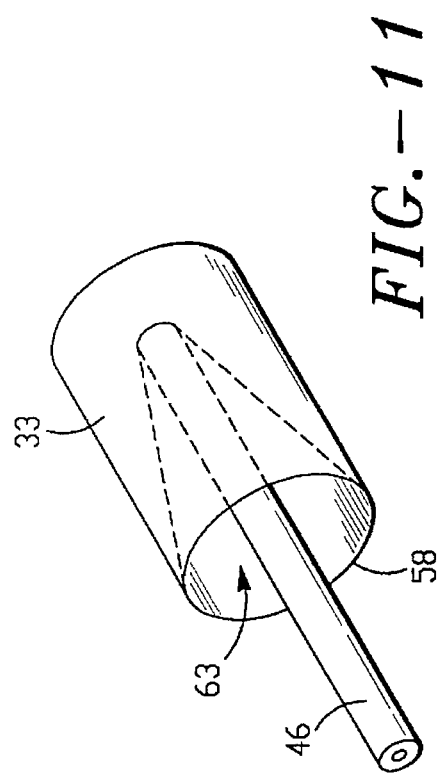
FIG. 11 is a diagonal view of a modified atheroma cutter on a drive cable.

FIGS. 10 and 11 illustrate another embodiment of the invention which includes a housing 28, a nose cone 52, a catheter body 22, a drive cable 46, and a modified cutter 33. In this embodiment, the orientation of the cutter 33 within the housing 28 is reversed relative to the embodiments described above, thereby allowing the excised tissue to be withdrawn from the catheter without removing the catheter from the artery.

The cutter 33 is mounted on the drive cable 46 such that its cutting edge 58 and open interior 63 face in the proximal direction, toward the drive cable 46. When operated within the housing 28, the cutter is axially translated past the aperture in a proximal direction to sever stenotic material. The cutter 33 is shown in a retracted position within a receiving space proximal of the perfusion ports 66.

Material

The elongated catheter body of the present invention typically comprises a flexible tube which can be similar in construction to a wide variety of intravascular catheters, the type of which are well known in the art. The flexible tube has a proximal end and a distal end and at least one lumen extending therebetween. The tube may be formed by extrusion of an organic polymer, typically a thermoplastic, such as nylon, polyethylene terephthalate (PET), polyvinylchloride (PVC), polyethylene, and the like. The tubes so formed can be reinforced or unreinforced, usually being reinforced by a metal braid which is laminated with a polymeric material. Use of the metal braid reinforcement layer is desirable since it facilitates torquing and positioning of the cutter housing. The catheter body has a length from about 40 cm to about 200 cm, with shorter catheters in the range from about 40 cm to 120 cm being used for peripheral applications, and longer catheters in the range from about 100 cm to 200 cm being used for coronary applications. The diameter of the catheter body may also vary, with smaller diameter catheters in the range from about 3French (F: 1F=0.33 mm) to 6F for coronary applications, and a diameter from 3F to 11F for peripheral applications.

The housing has a cylindrical structure with an elongated aperture along one side. The housing may be rigid or flexible, typically being formed from a metal, such as surgical stainless steel, nitinol or an organic polymer such as polyacetal, nylon or polyurethane. By rigid, it is meant that the housing has a generally continuous construction, usually composed of a metal or rigid plastic, including the side aperture, but free from other spacings or voids intended to enhance bendability. A flexible housing is formed from a resilient material, such as polyacetal, nylon or polyurethane, or if formed from a metal such as stainless steel or nitinol, includes spacings or voids which are intended to facilitate bending. The construction of particular flexible housings are illustrated in U.S. Pat. Nos. 4,781,186 and 5,312,425, the disclosures of which are incorporated herein by reference.

In an embodiment the catheter 20 is an atherectomy device. The open or hollow interior of the distal end of the housing 28 receives the severed stenotic material which penetrates or passes through the side aperture 54. The housing 28 receives an atheroma cutter 48 for severing the atheroma which penetrates into the interior and advances the severed material forward toward the distal end of the housing 28. The distal end of the housing is open and connected to a nose cone 52 so that the severed stenotic material can be moved into the nose cone for storage. FIGS. 3, 4, 6, 7 and 9 illustrate nose cones 52 having a mesh structure. The mesh may be metallic or polymeric, and permits outflow of blood from housing 28 through the mesh.

Such an atheroma cutter 48 is well illustrated in U.S. Pat. No. 4,979,951 and reissued U.S. Pat. No. Re. 33,569, the disclosures of which have previously been incorporated herein by reference.

The length of the housing 28 (FIG. 2) depends primarily on the desired length of stenotic material to be severed, with the limitation that longer housings are more difficult to manipulate through the vascular system. Typically, the length of the housing 28 is from 5 mm to 40 mm. For coronary applications, the housing length is generally at the shorter end of the range, usually being from about 8 mm to 17 mm. The housing diameter corresponds to the diameter of the flexible tube, i.e. usually being in the range from about 3F to 11F.

The aperture 54 (FIG. 2) of the housing 28 typically extends over at least half of the housing length. In another embodiment, the aperture 54 extends at least three-quarters of the length of the housing 28. In some embodiments it is desirable to maximize the length of the housing 28 in order to increase the area of the vessel which is exposed to intervention in the case of atherectomy catheters, and the amount of the stenotic material which can be removed in a single pass of the cutting blade, as described in more detail below.

In an alternative embodiment, the perfusion ports 66 (FIG. 6) are provided with weld rings mounted near the distal end of the catheter body 22. The weld rings 76 are welded to a metal reinforcement braid in the catheter body 22, with the perfusion ports 66 pre-drilled in the weld rings. After the weld rings have been welded to the braid, the material of the catheter body lying within the perfusion port 66 is removed.

Methods

According to the methods of the present invention, a portion of the universal catheter 20 (FIG. 1), starting from the distal end, is positioned in a blood vessel, such that the aperture 54 in the housing 28 is near a treatment site. The proximal assembly and a portion of the proximal end 26 of the catheter body 22 remain external to the patient. Typically, the apparatus is positioned over a movable guidewire 56 which has previously been positioned in the blood vessel as described above.

In an alternative method, once the housing is positioned proximate to the stenotic material within the blood vessel, the balloon 40 of the housing 28 (FIG. 1) is inflated to urge housing 28 against the vessel wall. This encourages the stenotic tissue through aperture 54 and into the hollow interior of the housing 28.

The work element 48 may or may not be positioned in the housing 28 when the catheter body 22 and housing 28 are positioned in the vessel. In one embodiment, the catheter body 22 and housing 28 are first positioned in a vessel without the work element 48 disposed in catheter body 22 or housing 28. Once the housing has been positioned near the treatment site, the work element 48 and connector 46 are inserted through catheter body lumen 64 of the catheter body until cutter 48 is within housing 28.

Once the apparatus has been positioned and the work element is disposed in housing 28, a selected interventional task may be performed through aperture 54 on the treatment site.

For example, when the interventional task is cutting stenotic material, a cutter is used as a work element 48, and a drive cable is used as the work element connector 46. The cutter is operated by attaching the drive cable 46 to a drive motor coupled to spline 42, as illustrated in FIG. 1. The drive motor is actuated, rotating or reciprocating the cable 46 and the cutter. The axial advance lever 50 may then be used to translate cutter across aperture 54, severing stenotic material extending through the aperture. Usually, the stenotic material is translated into the distal end of housing 28 and/or nose cone 52, where the material is stored.

In another embodiment, a catheter with a modified cutter 33 (FIG. 10), mounted to the drive cable 46 such that its cutting edge 58 faces in the proximal direction toward the drive cable 46, is used. The blade is positioned distal to aperture 54 prior to placement of the housing proximate the stenotic material. After the stenotic material is protruded into the housing 28, the cutter is translated in the proximal direction toward the catheter body 22 and across the aperture 54, thereby severing stenotic material. Once stenotic material has been severed, the cutter may then be completely withdrawn from the housing 28 and from the catheter body 22, so as to remove the severed material from the vessel. A second work element may then be inserted into the universal catheter, extended into work position within the housing, and then operated. This method greatly reduces the risk that severed material might escape the housing and enter the bloodstream. This method also overcomes limitations based upon filling the capacity of the nose cone for stenotic material, and it assures that the nose cone is free of material that might inhibit perfusion of downstream tissue.

In another embodiment of the method of this invention, the work element 48 is withdrawn from the housing 28 into the axial lumen of catheter body 22 (FIG. 3), so that the work element is positioned proximal to perfusion ports 66 in the catheter body and/or the housing. Blood is thereby allowed to flow with less resistance into the catheter body lumen 64 and housing 28, exiting through aperture 54, exit ports 68 or nose cone 52 so as to perfuse tissue downstream of the housing. Various systems for providing perfusion bypass in atherectomy catheters are described in U.S. Pat. No. 5,507,795, and entitled "Catheter With Perfusion System", assigned to the assignee of the present invention, the complete disclosure of which has been previously incorporated herein by reference.

In another embodiment of the method of this invention, a first work element may be completely withdrawn from the housing 28 and the catheter body 22 while the housing and catheter body remain positioned in the vessel. Accordingly, if it is desired to interchange the first work element 48 with a second work element, preferably a different type of work element, for example, an ultrasonic imaging transducer, angioscope, laser ablation device, abrasive grinding device, or dilatation balloon, the first work element 48 is withdrawn through the catheter body lumen 64 and removed from the vessel. The desired second work element may then be inserted through the catheter body lumen 64 and positioned in housing 28 to perform the desired task.

In a further embodiment of the method of the invention the catheter 20 is positioned in a vessel as described above and the work element 48 is disposed through the aperture 54, outside of the housing 28 and catheter body 22. This method is useful with work elements such as thermal ablators, certain types of fiber optic scopes, medicinal applicators, and other work elements known to those skilled in the art.

While the foregoing detailed description has described a preferred embodiment of the universal catheter with interchangeable work element in accordance with this invention, it is to be understood that the above description is illustrative only and not limiting of the disclosed invention. Particularly, the specific details of the work element and work element connector can differ from those illustrated and described so long as the work element is removable from the housing and catheter body and interchange-able. It will be appreciated that the nose cone and proximal assembly can differ from that disclosed so long as the their function is compatible with the function of the work element. Thus the invention is to be limited only by the claims set forth below.

What is claimed is:

1. An intravascular catheter for use with an interchangeable work element, the catheter comprising:

a catheter body having a distal end, a proximal end and a lumen extending therebetween; and a housing having a hollow interior, an aperture on a lateral side thereof and an open proximal end connected to the distal end of the catheter body, the connection defining a junctional region; and the lumen of the catheter body and the hollow interior of the housing combining to create a receiving space;

a coupling element connecting the distal end of the catheter body and the proximal end of the housing, the coupling element comprising a tubular adapter surrounding the distal end of the catheter body and the proximal end of the housing, whereby, a work element may be inserted into the receiving space from the proximal end of the catheter body.

2. An intravascular catheter as set forth in claim 1, the catheter further comprising a work element disposed within the housing and attached to a work element connector disposed through the lumen of the catheter body, the work element connector having a distal end connected to the work element and a proximal end proximate to the proximal end of the catheter body.

3. An intravascular catheter as set forth in claim 2, wherein the work element is selected from the group consisting of a cutting device, an angioplasty balloon, an imaging device, a combined cutting and imaging device, a laser atherectomy device, a thermal ablation device, an electrosurgical device, an abrasive ablation device, and an ultrasonic transducing device.

4. An intravascular catheter as set forth in claim 2, wherein the work element is a rotary atheroma cutter with a cutting edge and the work element connector is a drive cable.

5. An intravascular catheter as set forth in claim 2, wherein the catheter contains at least one perfusion port proximate to the junctional region, and wherein the work element is retractable proximal to the perfusion port.

6. An intravascular catheter as set forth in claim 2, further comprising a proximal assembly connected to the proximal end of the catheter body.

7. An intravascular catheter as set forth in claim 6, wherein the proximal end includes a hemostasis valve for preventing backbleeding and introduction of air when the work elements are exchanged, inserted or withdrawn.

8. An intravascular catheter as set forth in claim 6, wherein the work element is an atheroma cutting device and the work element connector is a drive cable.

9. An intravascular catheter as set forth in claim 1 wherein the coupling element comprises a flared distal end of the catheter body.

10. A method of surgically intervening within a blood vessel lumen, the method comprising the steps of:

providing a universal catheter that includes:
 a catheter body having a distal end, a proximal end and a lumen extending therebetween,
 a housing having a hollow interior, an aperture on a lateral side thereof, and an open proximal end connected to the distal end of the catheter body, the connection defining a junctional region,
 a perfusion port proximate to the junctional region and the lumen of the catheter body and the hollow interior of the housing combining to create a receiving space for a work element;

selecting a first work element;

inserting the first work element into the receiving space from the proximal end of the catheter body;

inserting the universal catheter from its distal end into and along the blood vessel lumen until the aperture of the housing is opposing a site of interest; and retracting the first work element proximal to the perfusion port whereby blood is able to flow past the catheter operating the first work element.

11. The method of surgically intervening within a blood vessel as set forth in claim 10, wherein insertion of the catheter within the blood vessel lumen is preceded by insertion of a guidewire within the blood vessel lumen proximate to the site of interest, and wherein the catheter is positioned within the blood vessel by sliding the catheter distally along the guidewire with the guidewire passing through the lumen of the catheter body.

12. The method of surgically intervening within a blood vessel as set forth in claim 10, wherein the universal catheter further includes a perfusion port proximate to the junctional region and the method further comprises positioning the first work element proximal to the perfusion port whereby blood is able to flow past the catheter.

13. The method of surgically intervening within a blood vessel as set forth in claim 12, further comprising the steps of selecting a second work element, inserting the second work element in the proximal end of the catheter body, positioning the second work element within the housing, and operating the second work element.

14. The method of surgically intervening within a blood vessel as set forth in claim 10, further comprising removal of the first work element from the proximal end of the catheter body while the catheter body and housing remain in place within the blood vessel.

15. A method of surgically intervening within a blood vessel as set forth in claim 14, wherein the second work element is selected to perform a function different from that of the first work element.

16. A method of surgically intervening within a blood vessel lumen, the method comprising the steps of:

providing a universal catheter including
 a catheter body having a distal end, a proximal end and a lumen extending therebetween,
 a housing having a hollow interior, an aperture on a lateral side thereof, and an open proximal end connected to the distal end of the catheter body, the connection defining a junctional region, and
 a drive cable disposed through the catheter body lumen and extending beyond the distal end of the catheter body into the hollow interior of the housing, and
 a rotary atheroma cutter with a cutting edge, the cutter being disposed within the housing and attached to the drive cable, and the cutter oriented such that the cutting edge faces the drive cable;

inserting the universal catheter from its distal end into and along the blood vessel lumen until the aperture of the housing is opposing a site with stenotic material on an interior wall of the blood vessel;

axially translating the cutter past the housing aperture and toward the catheter body, severing the stenotic material thereby and;

removing the cutter from the proximal end of the catheter body while the catheter body and housing remain in place within the blood lumen.

17. The method of surgically intervening within a blood vessel as set forth in claim 16, further comprising the steps of selecting a second work element, inserting the second work element in the proximal end of the catheter body, positioning the second work element within the housing, and operating the second work element.

18. A method of surgically intervening within a blood vessel lumen, the method comprising the steps of:

providing a universal catheter including:
 a catheter body having a distal end, a proximal end and a lumen extending therebetween, a housing having a hollow interior, an aperture on a lateral side thereof, and an open proximal end connected to the distal end of the catheter body, the connection defining a junctional region, and the lumen of the catheter body and the hollow interior of the housing combining to create a receiving space for a work element;

selecting a first work element;

inserting the first work element into the receiving space from the proximal end of the catheter body;

removing the first work element from the proximal end of the catheter body while the catheter body and housing remain in place within the blood vessel selecting a second work element inserting the universal catheter from its distal end into and along the blood vessel lumen until the aperture of the housing is opposing a site of interest; and operating either the first or the second work element as appropriate.

19. The method of surgically intervening within a blood vessel as set forth in claim 18, wherein insertion of the catheter within the blood vessel is preceded by insertion of a guidewire within the blood vessel proximate to the site of interest, and wherein the catheter is positioned within the blood vessel by sliding the catheter distally along the guidewire with the guidewire passing through the lumen of the catheter body.

20. A method of surgically intervening within a blood vessel as set forth in claim 18, wherein the first work element is selected from the group which additionally includes a drug delivery device, an aspirating device and hydraulic cutting/aspirating device.

21. The method of surgically intervening within a blood vessel as set forth in claim 20, further comprising removal of the first work element from the proximal end of the catheter body while the catheter body and housing remain in place within the blood vessel.

22. A method of surgically intervening within a blood vessel as set forth in claim 18, wherein the first work element is selected from the group consisting of a cutting device, an angioplasty balloon, an imaging device, a combined cutting and imaging device, a laser atherectomy device, a thermal ablation device, an electrosurgical device, an abrasive ablation device, and a ultrasonic transducing device.

23. The method of surgically intervening within a blood vessel as set forth in claim 22, further comprising the steps of selecting a second work element, inserting the second work element in the proximal end of the catheter body, positioning the second work element within the housing, and operating the second work element.

24. The method of surgically intervening within a blood vessel lumen as set forth in claim 23, wherein insertion of the universal catheter within the blood vessel lumen is preceded by insertion of a guidewire within the blood vessel lumen proximate to the stenotic material, and wherein the universal catheter is positioned within the blood vessel lumen by sliding the catheter distally along the guidewire with the guidewire passing through the lumen of the catheter body.

25. The method of surgically intervening within a blood vessel as set forth in claim 18, wherein the universal catheter further includes a perfusion port proximate to the junctional region and wherein the method further comprises positioning the first work element proximal to the perfusion port whereby blood is able to flow past the catheter.

26. The method of surgically intervening within a blood vessel as set forth in claim 25, wherein the second work element is selected to perform a function different from that of the first work element.

* * * * *